US012508387B2

(12) United States Patent
Barlow

(10) Patent No.: US 12,508,387 B2
(45) Date of Patent: Dec. 30, 2025

(54) PATIENT INTERFACE SYSTEMS

(71) Applicant: ResMed Pty Ltd, Bella Vista (AU)

(72) Inventor: Adam Francis Barlow, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 52 days.

(21) Appl. No.: 18/359,927

(22) Filed: Jul. 27, 2023

(65) Prior Publication Data

US 2023/0364372 A1 Nov. 16, 2023

Related U.S. Application Data

(63) Continuation of application No. 17/100,127, filed on Nov. 20, 2020, now Pat. No. 11,752,293, which is a continuation of application No. 16/015,388, filed on Jun. 22, 2018, now Pat. No. 10,869,982, which is a continuation of application No. 14/534,251, filed on Nov. 6, 2014, now Pat. No. 10,029,063, which is a continuation of application No. 13/372,792, filed on Feb. 14, 2012, now Pat. No. 8,905,031, which is a continuation-in-part of application No. 12/478,537, filed on Jun. 4, 2009, now Pat. No. 8,291,906.

(60) Provisional application No. 61/552,064, filed on Oct. 27, 2011, provisional application No. 61/457,272, filed on Feb. 16, 2011, provisional application No. 61/080,847, filed on Jul. 15, 2008, provisional application No. 61/058,659, filed on Jun. 4, 2008.

(51) Int. Cl.
*A61M 16/06* (2006.01)

(52) U.S. Cl.
CPC .... *A61M 16/0688* (2014.02); *A61M 16/0611* (2014.02); *A61M 16/0666* (2013.01); *A61M 16/0683* (2013.01); *A61M 2205/0216* (2013.01)

(58) Field of Classification Search
CPC .............. A61M 16/06; A61M 16/0605; A61M 16/0611; A61M 16/0616; A61M 16/0666; A61M 16/0672; A61M 16/0683; A61M 16/0688
See application file for complete search history.

(56) References Cited

U.S. PATENT DOCUMENTS 443,191 A 12/1890 Illing
781,516 A 1/1905 Guthrie, Jr.
(Continued)

FOREIGN PATENT DOCUMENTS

AU 199651130 10/1996
AU 2005100738 11/2005
(Continued)

OTHER PUBLICATIONS

Joel W. Beam, "Tissue Adhesives for Simple Traumatic Lacerations," Journal of Athletic Training, 2008, vol. 43, No. 2, pp. 222-224.
(Continued)

*Primary Examiner* — Joseph D. Boecker
(74) *Attorney, Agent, or Firm* — Nixon & Vanderhye P.C.

(57) ABSTRACT

A patient interface system includes a nasal seal of flexible material to communicate with at least one airway of the patient, and a primary headgear from which the nasal seal is suspended, said primary headgear having at least one aperture though which at least a portion of the nasal seal is inserted with the primary headgear wrapping about at least one portion of the nasal seal in a sling-like fashion.

20 Claims, 12 Drawing Sheets

(56) References Cited

U.S. PATENT DOCUMENTS 1,081,745 A 12/1913 Johnston
1,125,542 A 1/1915 Humphries
1,192,186 A 7/1916 Greene
1,229,050 A 6/1917 Donald
1,282,527 A 10/1918 Bidonde
1,362,766 A 12/1920 Mcgargill
1,445,010 A 2/1923 Feinberg
1,610,793 A 12/1926 Kaufman
1,873,160 A 8/1932 Sturtevant
2,353,643 A 7/1944 Bulbulian
2,415,846 A 2/1947 Randall
2,433,565 A 12/1947 Korman
2,625,155 A 1/1953 Engelder
2,706,983 A 4/1955 Matheson et al.
2,931,356 A 4/1960 Schwarz
3,013,556 A 12/1961 Galleher
3,670,726 A 6/1972 Mahon et al.
3,682,171 A 8/1972 Dali
3,739,774 A 6/1973 Gregory
3,754,552 A 8/1973 King
3,861,385 A 1/1975 Carden
3,902,486 A 9/1975 Guichard
3,905,361 A 9/1975 Hewson et al.
3,938,614 A 2/1976 Ahs
3,972,321 A 8/1976 Proctor
4,006,744 A 2/1977 Steer
4,142,527 A 3/1979 Garcia
4,153,051 A 5/1979 Shippert
4,156,426 A 5/1979 Gold
4,248,218 A 2/1981 Fischer
4,263,908 A 4/1981 Mizerak
4,264,743 A 4/1981 Maruyama et al.
4,267,845 A 5/1981 Robertson, Jr. et al.
4,273,124 A 6/1981 Zimmerman
4,312,359 A 1/1982 Olson
4,317,240 A 3/1982 Angerman
4,367,735 A 1/1983 Dali
4,367,816 A 1/1983 Wilkes
4,406,283 A 9/1983 Bir
4,414,973 A 11/1983 Matheson et al.
4,422,456 A 12/1983 Teip
4,449,526 A 5/1984 Elam
4,455,675 A 6/1984 Bose et al.
4,493,614 A 1/1985 Chu et al.
4,548,200 A 10/1985 Wapner
4,549,542 A 10/1985 Chien
4,572,323 A 2/1986 Randall
4,587,967 A 5/1986 Chu et al.
4,601,465 A 7/1986 Roy
4,603,692 A * 8/1986 Montesi ............... A62B 18/084 128/207.11
4,617,637 A 10/1986 Chu et al.
4,630,604 A 12/1986 Montesi
4,641,647 A 2/1987 Behan
4,660,555 A 4/1987 Payton
4,671,271 A 6/1987 Bishop et al.
4,676,241 A 6/1987 Webb et al.
4,699,139 A 10/1987 Marshall et al.
4,706,664 A 11/1987 Snook et al.
4,711,636 A 12/1987 Bierman
4,713,844 A 12/1987 Westgate
D293,613 S 1/1988 Wingler
4,753,233 A 6/1988 Grimes
4,767,411 A 8/1988 Edmunds
4,774,946 A 10/1988 Ackerman et al.
4,782,832 A 11/1988 Trimble et al.
4,790,829 A 12/1988 Bowden et al.
4,802,857 A 2/1989 Laughlin
4,803,981 A 2/1989 Vickery
4,811,730 A 3/1989 Milano
4,830,138 A 5/1989 Palmaer et al.
4,838,878 A 6/1989 Kalt et al.
4,899,740 A 2/1990 Napolitano
4,907,584 A 3/1990 Mcginnis
4,915,105 A 4/1990 Lee
4,919,128 A 4/1990 Kopala et al.
4,919,654 A 4/1990 Kalt
4,932,943 A 6/1990 Nowak
4,944,310 A 7/1990 Sullivan
4,945,907 A 8/1990 Tayebi
4,960,121 A 10/1990 Nelson et al.
4,966,590 A 10/1990 Kalt
4,969,880 A 11/1990 Zamierowski
4,971,051 A 11/1990 Toffolon
4,976,698 A 12/1990 Stokley
4,989,599 A 2/1991 Carter
4,996,983 A 3/1991 Amrhein
5,000,173 A 3/1991 Zalkin et al.
5,005,571 A 4/1991 Dietz
5,020,163 A 6/1991 Aileo et al.
5,022,900 A 6/1991 Bar-Yona et al.
5,023,955 A 6/1991 Murphy, II et al.
5,025,805 A 6/1991 Nutter
5,038,772 A 8/1991 Kolbe et al.
5,042,478 A 8/1991 Kopala et al.
5,046,491 A 9/1991 Derrick
5,074,297 A 12/1991 Venegas
5,113,857 A 5/1992 Dickerman et al.
5,117,818 A 6/1992 Palfy
5,121,745 A 6/1992 Israel
5,127,397 A 7/1992 Kohnke
5,137,017 A 8/1992 Salter
5,138,722 A 8/1992 Urella et al.
D333,015 S 2/1993 Farmer et al.
5,188,101 A 2/1993 Tumolo
5,207,665 A 5/1993 Davis et al.
5,220,699 A 6/1993 Farris
5,243,709 A 9/1993 Sheehan et al.
5,243,971 A 9/1993 Sullivan et al.
5,245,995 A 9/1993 Sullivan et al.
5,261,893 A 11/1993 Zamierowski
5,263,939 A 11/1993 Wortrich
5,265,592 A 11/1993 Beaussant
5,265,595 A 11/1993 Rudolph
5,267,557 A 12/1993 Her-Mou
5,269,296 A 12/1993 Landis
5,271,391 A 12/1993 Graves
5,299,599 A 4/1994 Farmer et al.
5,304,146 A 4/1994 Johnson et al.
5,320,092 A 6/1994 Ryder
5,335,656 A 8/1994 Bowe et al.
5,349,949 A 9/1994 Schegerin
5,355,878 A 10/1994 Griffiths et al.
5,355,893 A 10/1994 Mick et al.
5,364,367 A 11/1994 Banks et al.
5,372,130 A 12/1994 Stem et al.
5,372,388 A 12/1994 Gargiulo
5,372,389 A 12/1994 Tam et al.
5,372,390 A 12/1994 Conway et al.
5,372,391 A 12/1994 Bast et al.
5,375,593 A 12/1994 Press
5,385,141 A 1/1995 Granatiero
5,394,568 A 3/1995 Brostrom et al.
5,396,885 A 3/1995 Nelson
5,398,676 A 3/1995 Press et al.
5,400,776 A 3/1995 Bartholomew
5,419,318 A 5/1995 Tayebi
5,425,359 A 6/1995 Liou
5,429,683 A 7/1995 Le Mitouard
5,437,267 A 8/1995 Weinstein et al.
5,441,046 A 8/1995 Starr et al.
5,462,528 A 10/1995 Roewer
5,477,852 A 12/1995 Landis et al.
5,488,948 A 2/1996 Dubruille et al.
5,509,409 A 4/1996 Weatherholt
5,513,634 A 5/1996 Jackson
5,513,635 A 5/1996 Bedi
5,526,806 A 6/1996 Sansoni
5,533,506 A 7/1996 Wood
5,538,000 A 7/1996 Rudolph
5,538,001 A 7/1996 Bridges
5,560,354 A 10/1996 Berthon-Jones et al.
5,570,684 A 11/1996 Behr
5,592,938 A 1/1997 Scarberry et al.

(56) References Cited

U.S. PATENT DOCUMENTS

| | | | |
|---|---|---|---|
| 5,623,923 | A | 4/1997 | Bertheau et al. |
| 5,647,357 | A | 7/1997 | Barnett et al. |
| 5,653,228 | A | 8/1997 | Byrd |
| 5,655,527 | A | 8/1997 | Scarberry et al. |
| 5,662,101 | A | 9/1997 | Ogden et al. |
| 5,682,881 | A * | 11/1997 | Winthrop .......... A61M 16/0858 128/911 |
| 5,704,345 | A | 1/1998 | Berthon-Jones et al. |
| 5,707,342 | A | 1/1998 | Tanaka |
| 5,724,965 | A | 3/1998 | Handke et al. |
| 5,735,272 | A | 4/1998 | Dillon |
| 5,740,799 | A | 4/1998 | Nielson |
| 5,752,511 | A | 5/1998 | Simmons et al. |
| 5,794,619 | A | 8/1998 | Edeiman et al. |
| 5,807,341 | A | 9/1998 | Heim |
| 5,842,469 | A | 12/1998 | Rapp et al. |
| 5,906,203 | A | 5/1999 | Klockseth et al. |
| 5,918,598 | A * | 7/1999 | Belfer ................ A41D 13/1192 128/206.25 |
| 5,921,239 | A * | 7/1999 | McCall ................. A61M 16/06 128/206.26 |
| 5,931,854 | A | 8/1999 | Dillon |
| 5,954,049 | A | 9/1999 | Foley et al. |
| 5,975,079 | A | 11/1999 | Hellings et al. |
| 6,019,101 | A | 2/2000 | Cotner et al. |
| 6,026,811 | A | 2/2000 | Settle |
| 6,044,844 | A | 4/2000 | Kwok et al. |
| 6,050,260 | A | 4/2000 | Daniell et al. |
| 6,082,360 | A | 7/2000 | Rudolph et al. |
| 6,086,118 | A | 7/2000 | Mcnaughton et al. |
| 6,093,169 | A | 7/2000 | Cardoso |
| 6,095,996 | A | 8/2000 | Steer et al. |
| 6,098,205 | A | 8/2000 | Schwartz et al. |
| 6,109,263 | A | 8/2000 | Feuchtgruber |
| 6,112,746 | A | 9/2000 | Kwok et al. |
| 6,119,693 | A | 9/2000 | Kwok et al. |
| 6,119,694 | A | 9/2000 | Correa |
| 6,123,071 | A | 9/2000 | Berthon-Jones et al. |
| 6,123,082 | A | 9/2000 | Berthon-Jones |
| 6,139,787 | A | 10/2000 | Harrison |
| 6,152,137 | A | 11/2000 | Schwartz et al. |
| 6,193,914 | B1 | 2/2001 | Harrison |
| 6,196,223 | B1 | 3/2001 | Belfer |
| 6,211,263 | B1 | 4/2001 | Cinelli et al. |
| 6,231,548 | B1 | 5/2001 | Bassett |
| 6,241,930 | B1 | 6/2001 | Harrison |
| 6,258,066 | B1 | 7/2001 | Urich |
| 6,295,366 | B1 | 9/2001 | Haller et al. |
| 6,328,038 | B1 | 12/2001 | Kessler |
| 6,341,606 | B1 | 1/2002 | Bordewick |
| 6,347,631 | B1 | 2/2002 | Hansen et al. |
| 6,357,441 | B1 | 3/2002 | Kwok et al. |
| 6,358,279 | B1 | 3/2002 | Tahi et al. |
| 6,374,826 | B1 | 4/2002 | Gunaratnam et al. |
| 6,412,487 | B1 | 7/2002 | Gunaratnam et al. |
| 6,412,488 | B1 | 7/2002 | Barnett et al. |
| 6,412,593 | B1 | 7/2002 | Jones |
| 6,419,660 | B1 | 7/2002 | Russo |
| 6,422,238 | B1 | 7/2002 | Lithgow |
| 6,423,036 | B1 | 7/2002 | Van Huizen |
| 6,431,172 | B1 | 8/2002 | Bordewick |
| 6,434,796 | B1 | 8/2002 | Speirs |
| 6,439,234 | B1 | 8/2002 | Curti et al. |
| 6,448,303 | B1 | 9/2002 | Paul |
| 6,467,482 | B1 | 10/2002 | Boussignac |
| 6,467,483 | B1 | 10/2002 | Kopacko et al. |
| 6,470,887 | B1 | 10/2002 | Martinez |
| 6,478,026 | B1 | 11/2002 | Wood |
| 6,482,178 | B1 | 11/2002 | Andrews et al. |
| 6,491,034 | B1 | 12/2002 | Gunaratnam et al. |
| 6,513,526 | B2 | 2/2003 | Kwok et al. |
| 6,530,373 | B1 | 3/2003 | Patron et al. |
| 6,532,961 | B1 | 3/2003 | Kwok et al. |
| 6,536,435 | B1 | 3/2003 | Fecteau et al. |
| 6,536,436 | B1 | 3/2003 | Mcglothen |
| 6,561,188 | B1 | 5/2003 | Ellis |
| 6,561,190 | B1 | 5/2003 | Kwok et al. |
| 6,561,192 | B2 | 5/2003 | Palmer |
| 6,561,193 | B1 | 5/2003 | Noble |
| 6,571,798 | B1 | 6/2003 | Thornton |
| 6,579,267 | B2 | 6/2003 | Lynch et al. |
| 6,581,601 | B2 | 6/2003 | Ziaee |
| 6,581,602 | B2 | 6/2003 | Kwok et al. |
| 6,584,975 | B1 | 7/2003 | Taylor |
| 6,595,214 | B1 | 7/2003 | Hecker et al. |
| 6,595,215 | B2 | 7/2003 | Wood |
| 6,607,516 | B2 | 8/2003 | Cinelli et al. |
| 6,627,289 | B1 | 9/2003 | Dilnik et al. |
| 6,631,718 | B1 | 10/2003 | Lovell |
| 6,634,358 | B2 | 10/2003 | Kwok et al. |
| 6,637,434 | B2 | 10/2003 | Noble |
| 6,644,315 | B2 | 11/2003 | Ziaee |
| 6,655,385 | B1 | 12/2003 | Curti et al. |
| 6,663,600 | B2 | 12/2003 | Bierman et al. |
| 6,669,712 | B1 | 12/2003 | Cardoso |
| D485,905 | S | 1/2004 | Moore et al. |
| 6,679,257 | B1 | 1/2004 | Robertson et al. |
| 6,679,265 | B2 | 1/2004 | Strickland et al. |
| 6,701,927 | B2 | 3/2004 | Kwok et al. |
| 6,710,099 | B2 | 3/2004 | Cinelli et al. |
| 6,766,800 | B2 | 7/2004 | Chu et al. |
| 6,766,817 | B2 | 7/2004 | Da Silva |
| 6,776,162 | B2 | 8/2004 | Wood |
| 6,776,163 | B2 | 8/2004 | Dougill et al. |
| 6,789,543 | B2 | 9/2004 | Cannon |
| 6,805,117 | B1 | 10/2004 | Ho et al. |
| 6,807,967 | B2 | 10/2004 | Wood |
| 6,817,362 | B2 | 11/2004 | Gelinas et al. |
| 6,820,617 | B2 | 11/2004 | Robertson et al. |
| 6,823,865 | B2 | 11/2004 | Drew et al. |
| 6,823,869 | B2 | 11/2004 | Raje et al. |
| 6,834,650 | B1 | 12/2004 | Fini |
| 6,860,270 | B2 | 3/2005 | Sniadach |
| 6,895,965 | B2 | 5/2005 | Scarberry et al. |
| 6,907,882 | B2 | 6/2005 | Ging et al. |
| 6,918,404 | B2 | 7/2005 | Dias Da Silva |
| 6,926,004 | B2 | 8/2005 | Schumacher |
| 6,938,620 | B2 | 9/2005 | Payne, Jr. |
| 6,968,844 | B2 | 11/2005 | Liland |
| 6,972,003 | B2 | 12/2005 | Bierman et al. |
| 6,986,352 | B2 | 1/2006 | Frater et al. |
| 6,997,177 | B2 | 2/2006 | Wood |
| 7,011,090 | B2 | 3/2006 | Drew et al. |
| 7,018,362 | B2 | 3/2006 | Bierman et al. |
| 7,052,127 | B2 | 5/2006 | Harrison |
| 7,059,328 | B2 | 6/2006 | Wood |
| 7,066,586 | B2 | 6/2006 | Da Silva |
| 7,076,282 | B2 | 7/2006 | Munro et al. |
| 7,080,645 | B2 | 7/2006 | Genger et al. |
| 7,101,359 | B2 | 9/2006 | Kline et al. |
| 7,107,989 | B2 | 9/2006 | Frater et al. |
| 7,146,976 | B2 | 12/2006 | Mckown |
| 7,152,599 | B2 | 12/2006 | Thomas |
| 7,152,601 | B2 | 12/2006 | Barakat et al. |
| 7,156,097 | B2 | 1/2007 | Cardoso |
| 7,178,525 | B2 | 2/2007 | Matula, Jr. et al. |
| 7,191,781 | B2 | 3/2007 | Wood |
| 7,201,169 | B2 | 4/2007 | Wilkie et al. |
| 7,207,328 | B1 | 4/2007 | Altemus |
| 7,210,481 | B1 | 5/2007 | Lovell et al. |
| 7,237,551 | B2 | 7/2007 | Ho et al. |
| 7,243,723 | B2 | 7/2007 | Surjaatmadja |
| D550,836 | S | 9/2007 | Chandran et al. |
| D552,733 | S | 10/2007 | Criscuolo et al. |
| 7,285,255 | B2 | 10/2007 | Kadlec et al. |
| 7,302,950 | B2 | 12/2007 | Berthon-Jones et al. |
| 7,318,437 | B2 | 1/2008 | Gunaratnam et al. |
| 7,523,754 | B2 | 4/2009 | Lithgow |
| 7,658,189 | B2 | 2/2010 | Davidson |
| 8,291,906 | B2 | 10/2012 | Kooij |
| 8,905,031 | B2 * | 12/2014 | Barlow ............. A61M 16/0683 128/206.25 |
| 10,029,063 | B2 | 7/2018 | Barlow |
| 10,869,982 | B2 | 12/2020 | Barlow |

(56) References Cited

U.S. PATENT DOCUMENTS 11,752,293 B2 * 9/2023 Barlow .............. A61M 16/0611 128/205.25
2001/0020474 A1 9/2001 Hecker et al.
2002/0005198 A1 1/2002 Kwok et al.
2002/0029780 A1 3/2002 Frater et al.
2002/0046755 A1 4/2002 Devoss
2002/0053347 A1 5/2002 Ziaee
2002/0059935 A1 5/2002 Wood
2002/0066452 A1 6/2002 Kessler et al.
2002/0069872 A1 6/2002 Gradon et al.
2002/0096178 A1 7/2002 Ziaee
2002/0124849 A1 9/2002 Billette De Villemeur
2002/0143296 A1 10/2002 Russo
2002/0157673 A1 10/2002 Kessler
2002/0174868 A1 11/2002 Kwok et al.
2002/0175134 A1 11/2002 Hall
2002/0185134 A1 12/2002 Bishop
2003/0000526 A1 1/2003 Goebel
2003/0000533 A1 * 1/2003 Olsen ................ A61M 16/1095 128/206.21
2003/0019495 A1 1/2003 Palkon et al.
2003/0062048 A1 * 4/2003 Gradon ............. A61M 16/1075 128/207.11
2003/0079749 A1 5/2003 Strickland et al.
2003/0089373 A1 5/2003 Gradon et al.
2003/0111080 A1 6/2003 Olsen et al.
2003/0154980 A1 8/2003 Berthon-Jones et al.
2003/0168063 A1 9/2003 Gambone et al.
2003/0196656 A1 10/2003 Moore et al.
2003/0196658 A1 10/2003 Ging et al.
2003/0209246 A1 11/2003 Schroeder et al.
2004/0016432 A1 1/2004 Genger et al.
2004/0025882 A1 2/2004 Madaus et al.
2004/0025885 A1 2/2004 Payne, Jr.
2004/0045551 A1 3/2004 Eaton et al.
2004/0065328 A1 4/2004 Amarasinghe et al.
2004/0106891 A1 6/2004 Langan et al.
2004/0111104 A1 6/2004 Schein et al.
2004/0112384 A1 6/2004 Lithgow et al.
2004/0118406 A1 6/2004 Lithgow et al.
2004/0127856 A1 7/2004 Johnson
2004/0200476 A1 10/2004 Bamford
2004/0211428 A1 10/2004 Jones
2004/0226564 A1 11/2004 Persson
2004/0226566 A1 11/2004 Gunaratnam et al.
2004/0245658 A1 12/2004 Niland et al.
2005/0011523 A1 1/2005 Aylsworth et al.
2005/0028822 A1 2/2005 Sleeper et al.
2005/0033247 A1 2/2005 Thompson
2005/0034730 A1 2/2005 Wood
2005/0039757 A1 2/2005 Wood
2005/0051171 A1 3/2005 Booth
2005/0051176 A1 3/2005 Riggins
2005/0056286 A1 3/2005 Huddart et al.
2005/0061326 A1 3/2005 Payne
2005/0101933 A1 5/2005 Marrs et al.
2005/0109342 A1 * 5/2005 Easom .............. A61M 16/0683 128/206.12
2005/0150495 A1 7/2005 Rittner et al.
2005/0155604 A1 7/2005 Ging et al.
2005/0199242 A1 9/2005 Matula
2005/0211252 A1 9/2005 Lang et al.
2005/0217681 A1 * 10/2005 Frank .................... A61F 5/3707 128/846
2005/0241644 A1 11/2005 Gunaratnam
2005/0284481 A1 12/2005 Meyer
2006/0028346 A1 2/2006 White
2006/0054169 A1 * 3/2006 Han .................. A61M 16/0683 128/207.18
2006/0060200 A1 3/2006 Ho et al.
2006/0081250 A1 4/2006 Bordewick et al.
2006/0081256 A1 4/2006 Palmer
2006/0095008 A1 5/2006 Lampropoulos et al.
2006/0095009 A1 5/2006 Lampropoulos et al.
2006/0118117 A1 6/2006 Berthon-Jones
2006/0124131 A1 6/2006 Chandran et al.
2006/0137690 A1 6/2006 Gunaratnam et al.
2006/0174887 A1 8/2006 Chandran et al.
2006/0207597 A1 9/2006 Wright
2006/0237017 A1 10/2006 Davidson et al.
2006/0283461 A1 12/2006 Lubke et al.
2007/0023044 A1 2/2007 Kwok et al.
2007/0125387 A1 6/2007 Zollinger et al.
2007/0144525 A1 6/2007 Davidson et al.
2007/0186930 A1 8/2007 Davidson et al.
2007/0272249 A1 11/2007 Chandran et al.
2007/0282272 A1 12/2007 Bannon et al.
2008/0004573 A1 1/2008 Kaufmann et al.
2008/0006277 A1 1/2008 Worboys et al.
2008/0047560 A1 2/2008 Veliss et al.
2008/0060649 A1 3/2008 Veliss et al.
2008/0065022 A1 3/2008 Kyvik et al.
2008/0105257 A1 5/2008 Klasek et al.
2008/0110469 A1 5/2008 Weinberg
2008/0190436 A1 8/2008 Jaffe et al.
2008/0200880 A1 8/2008 Kyvik et al.
2008/0230067 A1 * 9/2008 Kwok ............... A61M 16/0683 128/207.18
2008/0257354 A1 10/2008 Davidson et al.
2009/0044808 A1 2/2009 Guney et al.
2009/0078259 A1 3/2009 Kooij et al.
2009/0188507 A1 * 7/2009 LaCava ............. A61M 16/0683 128/207.13
2009/0223514 A1 9/2009 Smith et al.
2009/0223521 A1 * 9/2009 Howard ............ A61M 16/0638 128/206.23
2009/0223523 A1 * 9/2009 Chang ............... A61M 16/0616 128/207.11
2010/0000534 A1 1/2010 Kooij
2010/0018534 A1 1/2010 Veliss et al.
2010/0229872 A1 * 9/2010 Ho .................... A61M 16/0633 128/206.25
2010/0307502 A1 12/2010 Rummery et al.
2010/0319700 A1 * 12/2010 Ng ........................ A61M 16/20 128/206.28
2011/0083670 A1 * 4/2011 Walacavage ........ A61M 16/107 128/205.12
2011/0146685 A1 6/2011 Allan
2012/0111332 A1 5/2012 Gusky
2012/0138060 A1 6/2012 Barlow
2013/0000647 A1 1/2013 Holley
2013/0037030 A1 * 2/2013 Matula, Jr. ........ A61M 16/0666 128/205.25
2013/0112206 A1 5/2013 Buddharaju
2013/0152937 A1 * 6/2013 Jablonski .......... A61M 16/0875 128/205.25
2015/0059760 A1 3/2015 Barlow
2018/0296786 A1 10/2018 Barlow
2021/0069446 A1 3/2021 Barlow

FOREIGN PATENT DOCUMENTS

AU 2007/048174 A1 5/2007
DE 185017 5/1907
DE 30 11 900 10/1980
DE 146 688 2/1981
DE 37 19 009 12/1988
DE 39 27 038 2/1991
DE 297 23 101 7/1998
DE 197 03 526 A1 8/1998
DE 199 44 242 3/2001
DE 100 02 571 7/2001
DE 102 13 905 10/2002
DE 10 2004 055 433 11/2004
EP 0 288 937 11/1988
EP 0 427 474 5/1991
EP 0 466 960 A1 1/1992
EP 0 303 090 4/1992
EP 0 658 356 6/1995
EP 0 776 679 A1 6/1997
EP 1 099 452 5/2001
EP 1 258 266 11/2002

(56) References Cited

FOREIGN PATENT DOCUMENTS

| | | | | |
|---|---|---|---|---|
| EP | 1 481 702 | | 12/2004 | |
| FR | 2 720 280 | | 12/1995 | |
| FR | 2749176 | A1 * | 12/1997 | ............ A61M 16/06 |
| GB | 532214 | | 1/1941 | |
| GB | 2 176 404 | | 12/1986 | |
| GB | 2 368 533 | | 5/2002 | |
| GB | 2 385 533 | | 8/2003 | |
| GB | 2385533 | A * | 8/2003 | ............ A61M 16/06 |
| JP | 2005-87766 | | 4/2005 | |
| JP | 2005-304574 | | 11/2005 | |
| JP | 2009-502429 | | 1/2009 | |
| JP | 2009-545408 | | 12/2009 | |
| WO | WO 1982/003548 | | 10/1982 | |
| WO | WO 1987/001950 | | 4/1987 | |
| WO | WO 1992/020392 | | 11/1992 | |
| WO | WO 1992/020395 | | 11/1992 | |
| WO | WO 1996/028207 | | 9/1996 | |
| WO | WO 1998/004310 | | 2/1998 | |
| WO | WO 1998/012965 | | 4/1998 | |
| WO | WO 98/23305 | A1 | 6/1998 | |
| WO | WO 99/16327 | A1 | 4/1999 | |
| WO | WO 99/25410 | A1 | 5/1999 | |
| WO | WO 1999/043375 | | 9/1999 | |
| WO | WO 1999/061088 | | 12/1999 | |
| WO | WO 2000/020072 | | 4/2000 | |
| WO | WO 2000/038772 | | 7/2000 | |
| WO | WO-0050121 | A1 * | 8/2000 | ............ A61M 16/06 |
| WO | WO 00/64521 | A1 | 11/2000 | |
| WO | WO 2000/069521 | | 11/2000 | |
| WO | WO 2000/072905 | | 12/2000 | |
| WO | WO 2000/074758 | | 12/2000 | |
| WO | WO 2000/076568 | | 12/2000 | |
| WO | WO 2000/078384 | | 12/2000 | |
| WO | WO 2001/062326 | | 8/2001 | |
| WO | WO 2001/095965 | | 12/2001 | |
| WO | WO 2001/097892 | | 12/2001 | |
| WO | WO 2001/097893 | | 12/2001 | |
| WO | WO 02/38221 | A1 | 5/2002 | |
| WO | WO 2002/045784 | | 6/2002 | |
| WO | WO 2003/090827 | | 11/2003 | |
| WO | WO 2003/105921 | | 12/2003 | |
| WO | WO 2004/022146 | | 3/2004 | |
| WO | WO 2004/041342 | | 5/2004 | |
| WO | WO 2004/073778 | | 9/2004 | |
| WO | WO 2005/018524 | A2 | 3/2005 | |
| WO | WO 2005/053781 | | 6/2005 | |
| WO | WO 2005/063328 | | 7/2005 | |
| WO | WO 2005/086943 | | 9/2005 | |
| WO | WO 2005/099801 | | 10/2005 | |
| WO | WO 2005/110220 | | 11/2005 | |
| WO | WO 2005/118040 | | 12/2005 | |
| WO | PCT/AU2006/000031 | | 1/2006 | |
| WO | PCT/AU2006/000417 | | 3/2006 | |
| WO | PCT/AU2006/000770 | | 6/2006 | |
| WO | WO 2006/069415 | | 7/2006 | |
| WO | WO 2006/074513 | | 7/2006 | |
| WO | WO 2006/074516 | | 7/2006 | |
| WO | WO 2006/099658 | | 9/2006 | |
| WO | WO 2006/130903 | | 12/2006 | |
| WO | WO-2006130903 | A1 * | 12/2006 | ............ A61M 16/06 |
| WO | WO 2007/009182 | | 1/2007 | |
| WO | WO 2007/016424 | | 2/2007 | |
| WO | WO 2007/041751 | | 4/2007 | |
| WO | WO 2007/041786 | | 4/2007 | |
| WO | WO 2007/048174 | | 5/2007 | |
| WO | WO 2007/053878 | | 5/2007 | |
| WO | PCT/AU2007/001936 | | 12/2007 | |
| WO | WO 2007/143772 | A2 | 12/2007 | |
| WO | WO 2007/145534 | | 12/2007 | |
| WO | WO 2008/011682 | | 1/2008 | |
| WO | WO 2008/011683 | | 1/2008 | |
| WO | WO 2008/014543 | | 2/2008 | |
| WO | WO 2008/019294 | | 2/2008 | |
| WO | WO 2008/040050 | | 4/2008 | |
| WO | WO 2008/070929 | | 6/2008 | |
| WO | WO 2009/052560 | | 4/2009 | |
| WO | WO 2009/108994 | | 9/2009 | |
| WO | WO 2009/109004 | | 9/2009 | |
| WO | WO 2009/146484 | A1 | 12/2009 | |
| WO | WO 2010/028425 | | 3/2010 | |
| WO | WO 2010/0139014 | | 12/2010 | |

OTHER PUBLICATIONS

Extended European Search Report Mailed Sep. 3, 2009 in corresponding EP Application No. 09161984.1.
Webster's Third New International Dictionary, 1993, Dictionary definition for adjustable, bendable, and mild steel.
Comfortlite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
Extended European Search Report dated Mar. 19, 2009 in European Application No. EP 08161249.
Extended European Search Report. Application No. EP 08154854, dated Nov. 27, 2008.
Fisher and Paykel Col.—Product Family—http://www.fphcare.com/osa/products.asp/.
Hans Rudoplh, Inc.—Mask Products—http://www.rudolphkc.com/products.php?category=MASKS.
International Preliminary Report on Patentability for PCT/AU2004/001832, dated Jul. 3, 2006.
International Search Report for PC/AU2005/000803, dated Jun. 30, 2005.
Examination Report filed in New Zealand Application 539836, dated Aug. 25, 2005.
European Search Report issued in EP 07845378.4, mailed Dec. 1, 2009.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Merriam-Webster Online Dictionary definition of moveable from the 14th century.
Office Action mailed Dec. 22, 2009 in European Appln. No. 04802133.1.
ResMed Co.—Mask Products—http://resmed.com/portal/site/ResMedUS/index.jsp?. . . .
Respironics Co.—Mask Family—http://masksfamily.respironics.com/.
Examiner's Report No. 3 mailed Nov. 18, 2009 in New Zealand Application No. 2003275762.
Supplementary Search Report issued in European Appln. 05746824.1, dated Dec. 17, 2009.
Supplementary European Search Report mailed Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
Examination Report Mailed Feb. 28, 2011 in European Application No. 09 161 984.1 (4 pages).
Examination Report Mailed Dec. 8, 2010 in New Zealand Application No. 589634 (3 pages).
SNAPP Nasal Interface, Tiara Medical Systems, Inc.—http://www.tiaramed.com/asp_shops/shopdisplayproducts.asp?id=109&cat=SNAPP%2A+Nasal+Interface.

(56) References Cited

OTHER PUBLICATIONS

Supplementary European Search Report mailed Sep. 8, 2009 in European Appln. No. 04802133.1.
International Search Report filed in PCT/AU2006/000770, dated Aug. 3, 2006.
International Search Report for PCT/AU2007/001052, dated Oct. 9, 2007.
International Search Report for PCT/AU2006/000770, dated Jun. 30, 2005.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Notification of the Third Office Action and English Translation for corresponding Chinese Application No. 200910163947.3, issued Mar. 13, 2014, 11 pages.
Notification of the Fourth Office Action issued Oct. 10, 2014 in Chinese Application No. 200910163947.3, with English Translation (11 pages).
Decision of Rejection and English Translation for corresponding Japanese Application No. 2009-135413, mailed Dec. 24, 2013, 6 pages.
Notice of Reasons for Rejection and English Translation issued in corresponding Japanese Application No. 2009-135413, mailed Jul. 2, 2013, 7 pages.
Chinese Notification of First Office Action and English Translation for corresponding Chinese Application No. 200910163947.3, dated Dec. 13, 2012, 8 pages.
Australia Patent Examination Report No. 1 for corresponding Australian Application No. 2009202232, issued Sep. 4, 2012, 4 pages.
Adam J. Singer MD et al., "The Cyanoacrylate Topical Skin Adhesives," American Journal of Emergency Medicine, vol. 26, 2008, pp. 490-496.
Office Action issued in Chinese Application No. 200910163947.3 dated Aug. 29, 2013 (with translation).
Subbu Venkatraman et al., "Review Skin Adhesives and Skin Adhesion 1. Transdermal Drug Delivery Systems," Biomaterials, vol. 19, 1998, pp. 1119-1136.
Examination Report for corresponding New Zealand Application No. 589634, mailed Apr. 26, 2012, 2 pages.
"Ear Loop Face Mask".
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.

* cited by examiner

PATIENT INTERFACE SYSTEMS

CROSS REFERENCE TO RELATED APPLICATIONS

This application is a continuation of U.S. application Ser. No. 17/100,127, filed Nov. 20, 2020, which is a continuation of U.S. application Ser. No. 16/015,388, filed Jun. 22, 2018, now U.S. Pat. No. 10,869,982, which is a continuation of U.S. application Ser. No. 14/534,251, filed Nov. 6, 2014, now U.S. Pat. No. 10,029,063, which is a continuation of U.S. application Ser. No. 13/372,792 filed Feb. 14, 2012, now U.S. Pat. No. 8,905,031, which is a continuation-in-part of U.S. application Ser. No. 12/478,537 filed Jun. 4, 2009, now U.S. Pat. No. 8,291,906, which claims the benefit of U.S. Provisional Application Nos. 61/058,659 filed Jun. 4, 2008 and 61/080,847 filed Jul. 15, 2008, and this application also claims benefit of U.S. Provisional Application Nos. 61/457,272, filed Feb. 16, 2011 and 61/552,064 filed Oct. 27, 2011, each of which is incorporated by reference in its entirety.

FIELD OF THE TECHNOLOGY

The present technology relates to patient interface systems for delivery of a flow of breathable gas to a patient. The present technology also relates to patient interface systems that may include adhesive(s) to support the patient interface in engagement with the patient and/or a patient interface positioning and/or support structure.

BACKGROUND OF THE INVENTION

The use of positive airway pressure (PAP) for the treatment of sleep disordered breathing (SDB), such as obstructive sleep apnea (OSA), was disclosed in U.S. Pat. No. 4,944,310. Treatment using PAP, which may be continuous PAP (CPAP), involves the use of a patient interface which is attached to the patient's face for the provision of the flow of breathable gas. PAP treatment involving the use of a patient interface that is sealingly attached to the wearer's face may be referred to as closed PAP.

For patients that require treatment of OSA, a patient interface, e.g. a mask, that forms a seal with the patient's airways may be required. However, the patient may find adapting to current interfaces difficult. For example, the patient may have difficulty sleeping in a familiar, comfortable position once the mask, including the headgear and air delivery hose, are fitted to the patient to provide the required seal. Although the mask is capable of providing a seal and the prescribed pressure, the patient may be reluctant to use the mask due to the problem of sleeping comfortably while wearing the mask. The patient may also find the mask assembly too obtrusive. These factors may result in the patient abandoning the treatment.

SUMMARY OF THE TECHNOLOGY

One example of the present technology relates to the use of a silicone nasal or nares seal assembly and a relatively small headgear that may work in conjunction with an adhesive pad. The small headgear may be positioned, for example, between the nasal or nares seal and a gusset or connecting region of the nasal or nares seal assembly. The headgear may be attachable to the adhesive pad, e.g., by an attachment mechanism such as hook and loop material. The nasal or nares seal may be in the form of nasal prongs or nozzles, or it may be a nasal or nares seal that seals around both nares in the small region between or in the vicinity of the upper lip and the tip of the user's nose.

Another example of the present technology relates to a patient interface system comprising a nasal seal of flexible material to communicate with at least one airway of the patient; and a primary headgear from which the nasal seal is suspended, said primary headgear including a fabric and/or textile material having at least one aperture though which at least a portion of the nasal seal is inserted with the primary headgear wrapping about at least one portion of the nasal seal in a sling-like fashion. The headgear may work in conjunction with a securing pad that is secured to the patient's face, e.g., an adhesive pad that is adhesively secured to the nasal bridge region of the patient's face.

Another example of the present technology relates to a patient interface system comprising a nasal seal of flexible material to communicate with at least one airway of the patient, and a primary headgear to which the nasal seal is attached, said primary headgear including a fabric and/or textile material connected to at least a portion of the nasal seal, with the primary headgear removably attachable to an adhesive strip positioned on the patient.

Another example of the present technology relates to a patient interface system comprising a nasal seal of flexible material to communicate with at least one airway of the patient; and a primary headgear in which the nasal seal and primary headgear are positively located, inter-engaged, interlocked, intermeshed, sandwiched, and/or abutted against, etc., one another. For example, a portion of the nasal seal may extend through an aperture or slot, etc., in the primary headgear, and/or vice versa.

Another example of the present technology relates to a patient interface including an unobtrusive or low profile nasal seal (e.g., nozzles or a nares seal) that may be securely suspended from a relatively small headgear. The headgear and nasal seal are structured to inter-engage, etc. with one another, without requiring one or more separate clips to connect the headgear to the patient interface.

Another example of the present technology relates to a patient interface that can be suspended on a patient's face without any "hard" parts, such as a polycarbonate frame or "shell" to which many typical cushions are connected, and/or so-called headgear clips which allow connection between headgear straps and the frame/shell. For example, the patient interface may include a soft and complaint nasal seal (e.g., nasal only, oro-nasal, nozzles, prongs, nares seal, etc.), and a headgear made of soft and flexible material, e.g., composite materials such as laminated foam and fabric, a non woven fabric, a mesh, etc. The headgear may be suspended from a securing pad that can be adhesively or otherwise supported on the patient's face (e.g., nasal bridge).

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various sample embodiments, wherein.

DETAILED DESCRIPTION

The following description is provided in relation to several examples which may share common characteristics and features. It is to be understood that one or more features of any one example may be combinable with one or more features of the other examples. In addition, any single feature or combination of features in any of the examples may constitute an additional feature or features that may be independently claimed and pursued.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

As used herein, the term "patient interface system" refers to a structure configured to engage the face of a patient and deliver the flow of breathable gas to the patient's airways.

Examples of the present technology relate to the use of an existing or slightly modified silicone nasal or nares seal and a small headgear that may work in conjunction with a securing or adhesive pad. The small headgear may be positioned, for example, between a nasal or nares seal and a gusset, base or connecting region of the nasal or nares seal assembly. The headgear may be attachable to the adhesive pad, e.g., by an attachment mechanism such as hook and loop material, or adhesive. The nasal or nares seal may be in the form of nasal prongs or nozzles, or it may be a nasal or nares seal that seals around both nares in the small region between or in the vicinity of the upper lip and the tip of the user's nose, a shown, for example, in PCT/AU2010/000684 filed Jun. 2, 2010, incorporated by reference in its entirety.

Figure 1:
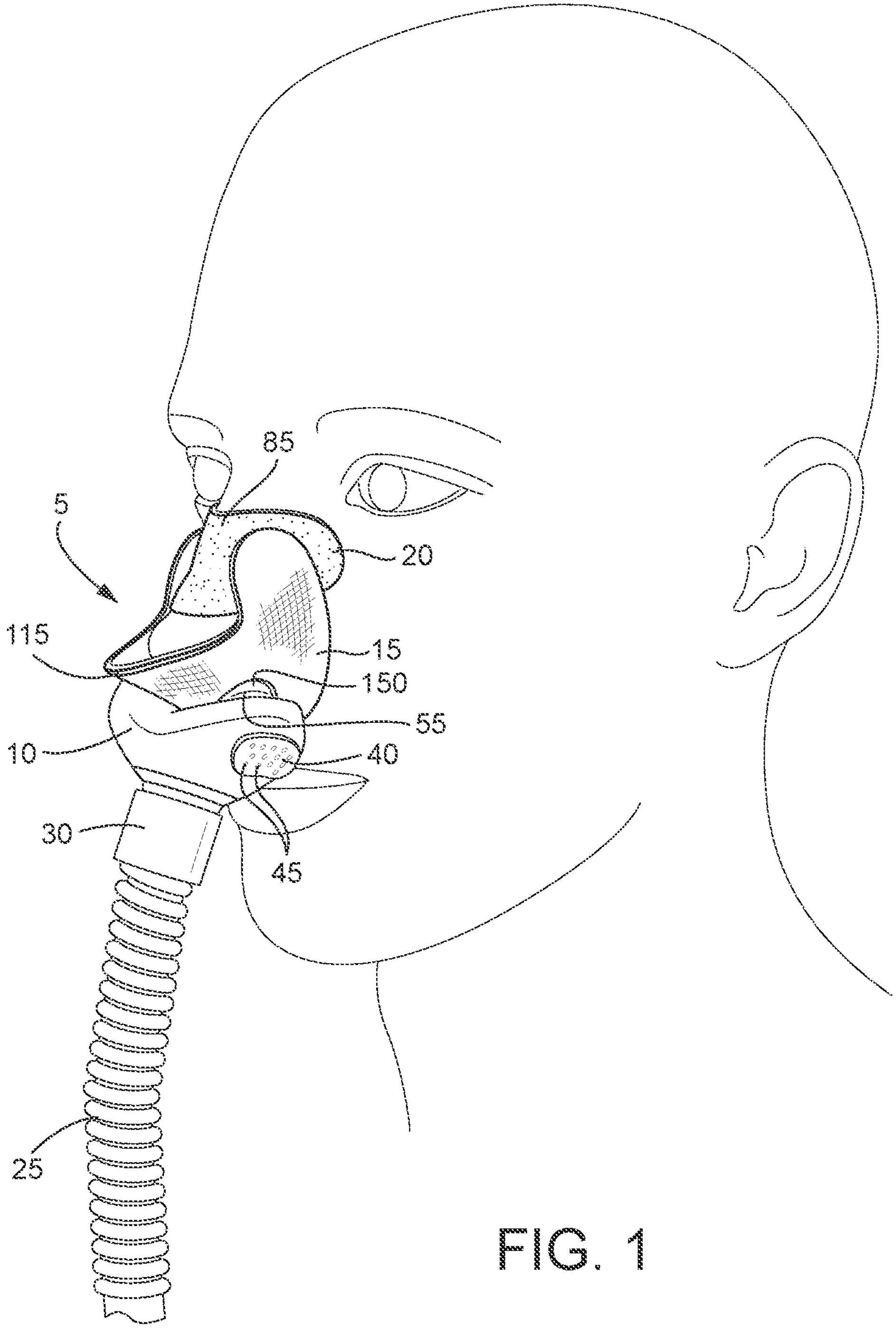
FIG. 1 is a perspective view of a patient interface system according to an example of the present technology in an operational position on a model patient's head.
Figure 2:
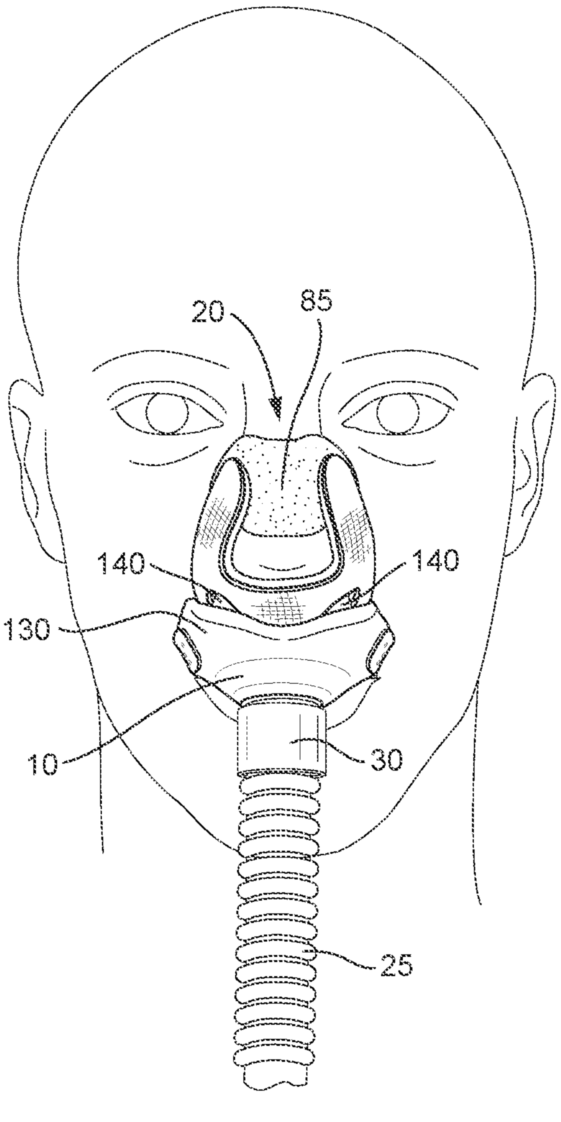
FIG. 2 is a front view thereof.
Figure 3:
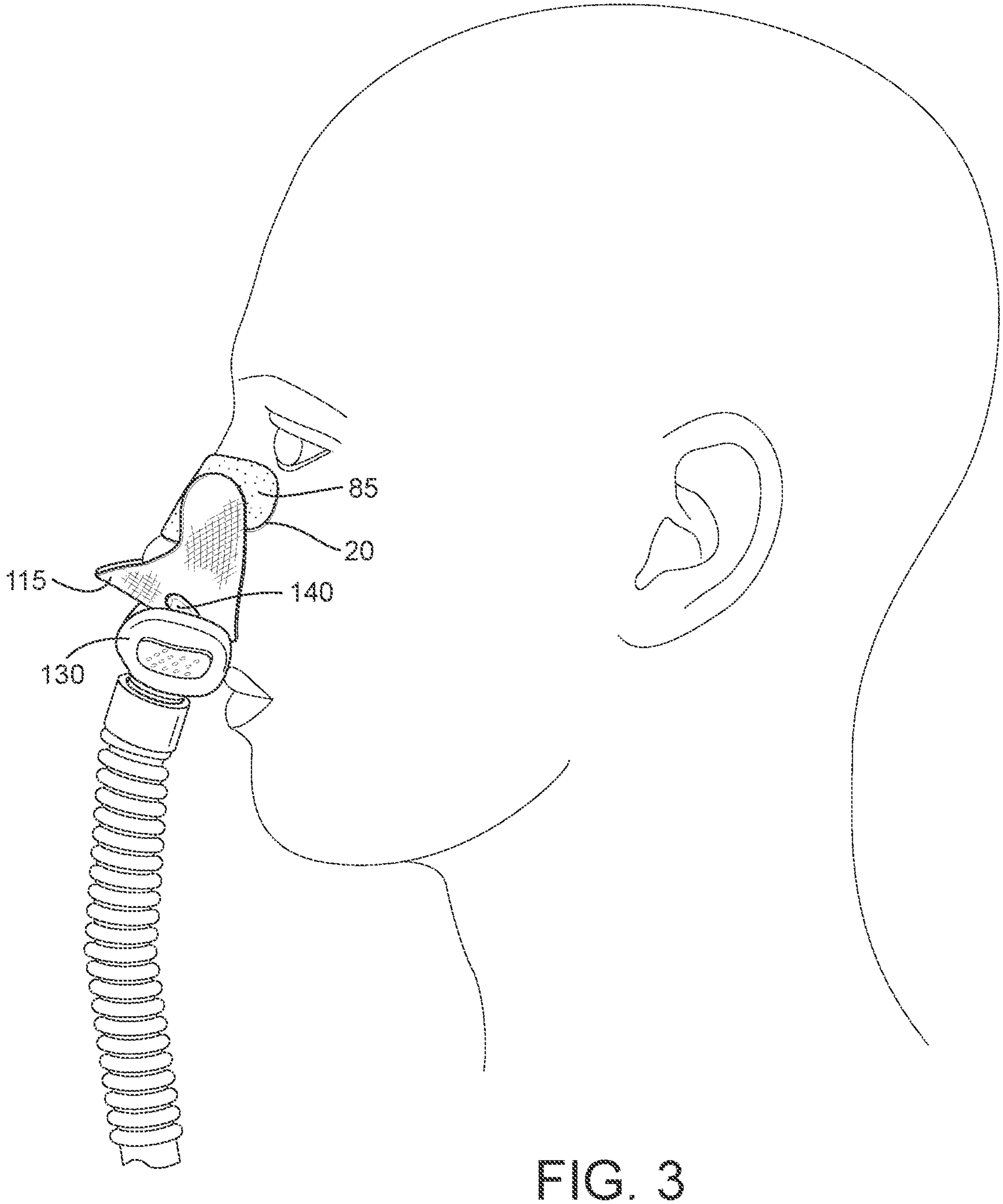
FIG. 3 is a side view thereof.

FIGS. 1-3 show a patient interface system 5 according to an example of the present technology. Patient interface system 5 includes a nasal seal 10 of flexible material, e.g., silicone or another elastomer, to communicate with at least one airway of the patient. A primary headgear 15 is provided from which the nasal seal 10 is suspended. The assembly or sub-combination of the nasal seal 10 and the primary headgear 15 may be suspended from the patient's head (e.g., nose), using a securing pad, e.g., an adhesive pad 20.

Figure 4:
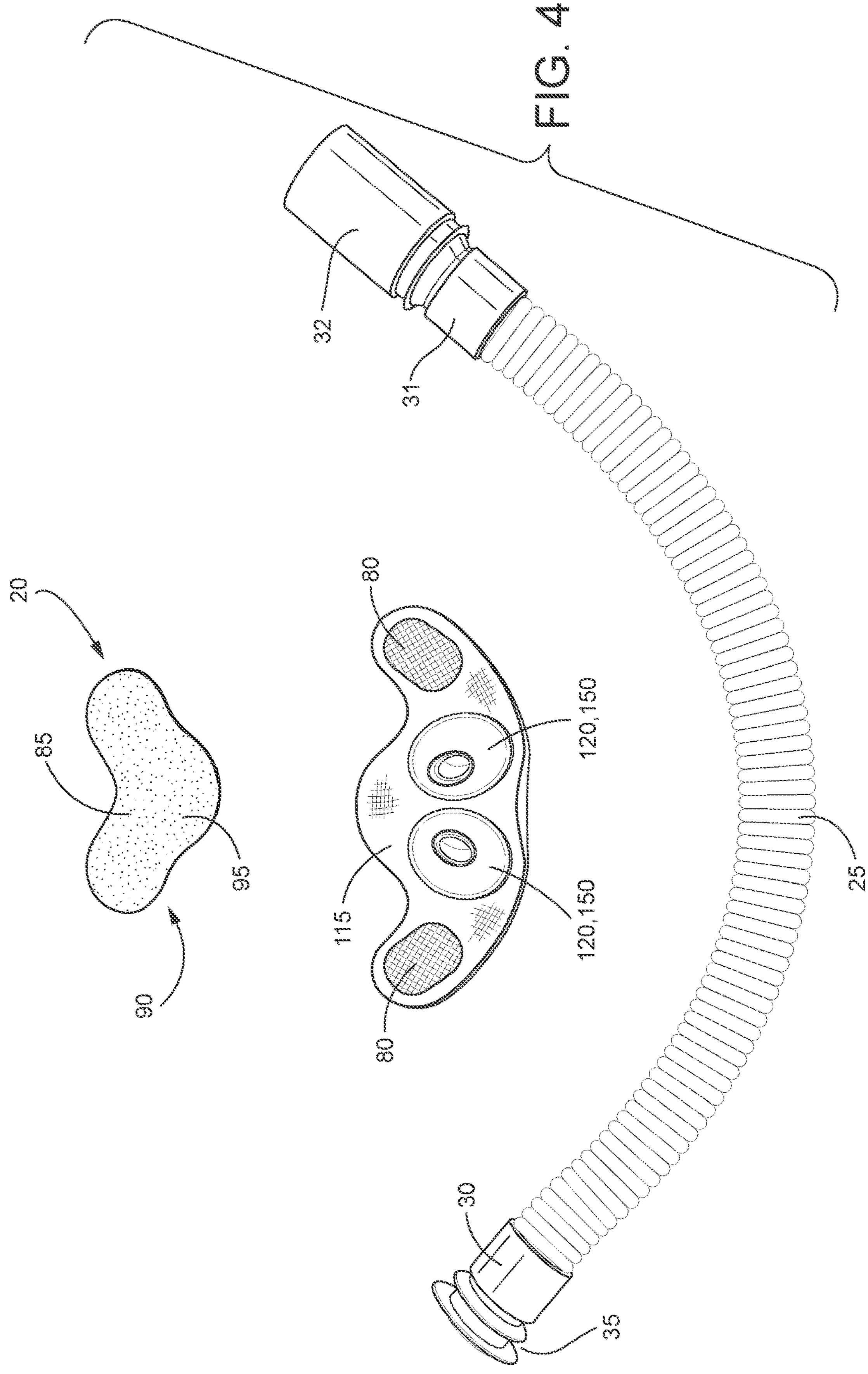
FIG. 4 is an exploded view of the patient interface system shown in FIGS. 1-3.
Figure 5:
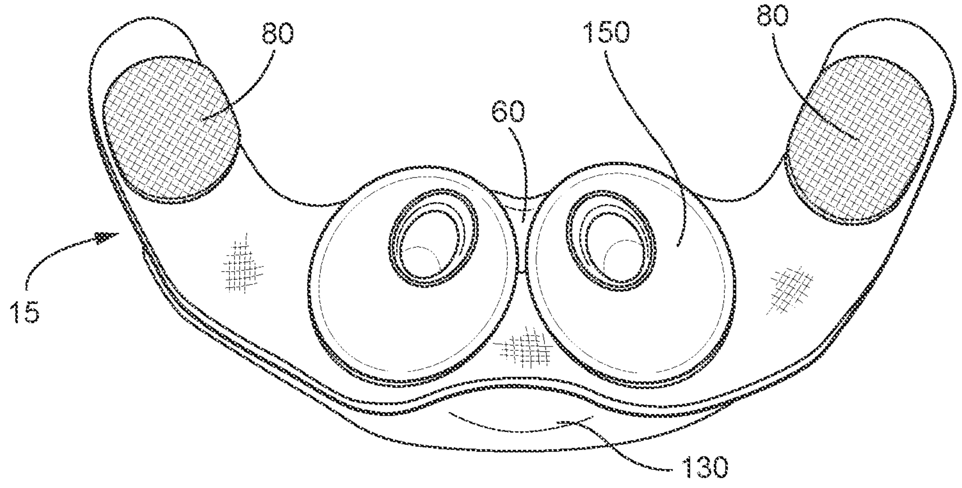
FIG. 5 is a top view of a nasal seal and primary headgear subassembly thereof.

The patient interface system 5 may include a short tube 25 having a first end 30 to connect with the nasal seal 10, and a second end 31 to connect with an air delivery tube via a swivel 32. The first end 30 of the short tube may include a gusset or decoupling joint 35 (FIG. 4) to accommodate for tube drag and rotational forces. The patient interface system may include a vent 40, e.g., a plurality of holes 45, to allow for $CO_2$ gas washout.

The primary headgear 15 includes a fabric and/or textile material or layer having at least one aperture 50 (FIG. 6) though which at least a portion 55 of the nasal seal 10 is inserted, with the primary headgear 15 wrapping about at least one portion (e.g., the nozzles) of the nasal seal in a sling-like fashion. The primary headgear 15 includes a center section 60 having the at least one aperture 50 through which the nozzle heads 150 of the nasal seal extend such that the nasal seal is positively located against a rim 65 surrounding the aperture 50. The at least one aperture 50 may include a reinforcement at least partially about the rim, e.g., stitching or a donut/torus shaped reinforcement, to prevent tearing/deformation.

The headgear 15 may be made from a laminate including multiple layers, e.g., a fabric and/or textile or textile and flexible polymeric material such as silicone; a soft, breathable and flexible patient contacting or facing inner layer such as fabric and/or textile, a soft and flexible outer layer and a foam-type layer between the inner and outer layers. The headgear may be reinforced with a stiffening material (e.g., plastic or nylon) to add rigidity in one or more regions. The primary headgear 15 is made of a soft and flexible material, such as that sold under the trade name "Breath-O-Prene".

In an alternative form, primary headgear 15 may be constructed from or constructed in part from a deformable plastic such as silicone, thermoplastic elastomer, etc. The deformable plastic may be able to change shape e.g. from a flat position to an in use curved position, be comfortable on the user's face, and receive nozzle heads 150. In a further example, the first attachment region 80 may be, for example, hook portions that are integrally molded with primary headgear 15. First attachment region 80 may be formed of the same material as primary headgear 15 or a different material than primary headgear 15. In a further example, primary headgear 15 may include a stiffer material in some portions for reinforcing, e.g. rims 65 may be lined with a substantially stiffer material than other regions of primary headgear 15. Such an arrangement may ensure structure integrity and prevent tearing or wear of the primary headgear in these stiffened regions. It may also aid in aligning and fitting primary headgear 15 to nozzle heads 150, and supporting nozzle heads 150 in position.

Figure 12:
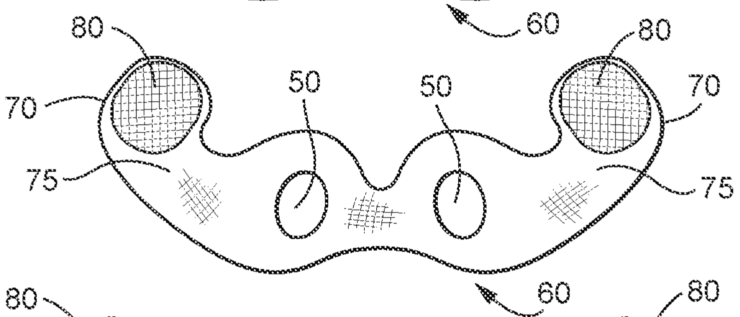
Figure 13:
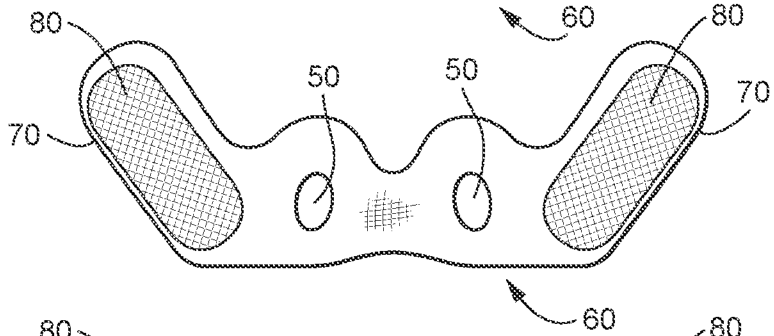
Figure 14:
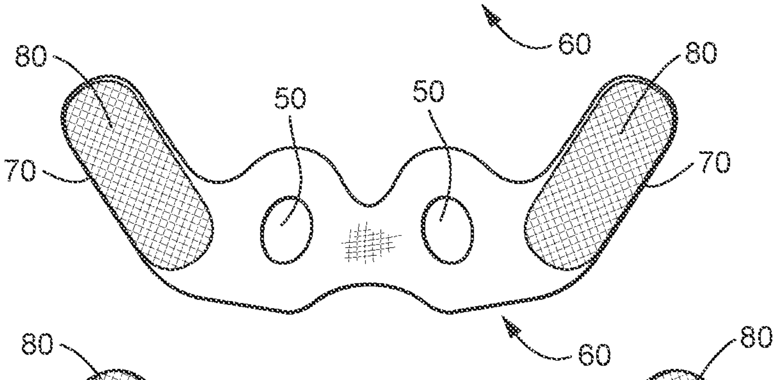

The primary headgear includes at least one arm 70 extending from the center section 60. Each arm 70 may extend away from the center section 60 linearly, or in a curved or curled fashion, and/or at an angle β (e.g., about 20°-140° from horizontal) relative to the center section as shown in the variants in FIGS. 10-21. This arrangement may enable arms 70 to be positioned on the flares or sides of the patient's nose in use, rather than positioning on the patient's cheeks or top lip. Alternatively, or in addition, each arm 70 may include a connection 75 provided between the center section 60 and the arm 70 (see for example FIGS. 12 and 15). Connection 75 may be a portion of fabric or other material that forms a bridge between the center section 60 and the arm 70. Connection 75 may include, for example, supplemental attachments for receiving a supplemental headgear. For example, connection 75 may include an eye and a supplemental headgear may include a hook, the eye adapted to receive the hook. Alternative removably attachable mechanisms may be possible, for example hook and loop, buttons, etc.

The primary headgear may include two or more arms 70 extending from the center section 60, e.g., a pair of laterally extending arms as shown in FIGS. 6 and 10-25. Each arm may include a first attachment region 80 provided at or near an end of each arm. Each first attachment region 80 may include a hook or loop type fastener, for attachment to a second attachment region, e.g., loop or a hook type fastener 85, provided on the securing or adhesive pad 20 provided to the patient's face. The securing pad may be supported on the patient's head with one or more straps.

The securing pad 20 may be in the form of an adhesive pad that has a first side 90 provided with an adhesive to adhesively contact the patient's face (e.g., nasal bridge region) and a second side 95 to engage or receive a portion (e.g., the arm(s)) of the primary headgear. The second side 95 may include a second attachment region to engage with the first attachment region 80. The first and second attachment regions may be secured to one another via a hook and loop fastening system. However, the first and second attachment regions may be secured to one another via alternative means, for example adhesive, hook and eye clasp.

Alternatively, each first attachment region 80 may include an adhesive to adhere directly to the patient's face in use, in which case the adhesive pad 20 may not be required. In addition, the first attachment region 80 may be in the form of a clip that is received within a receiving portion of the pad 20.

Figure 6:
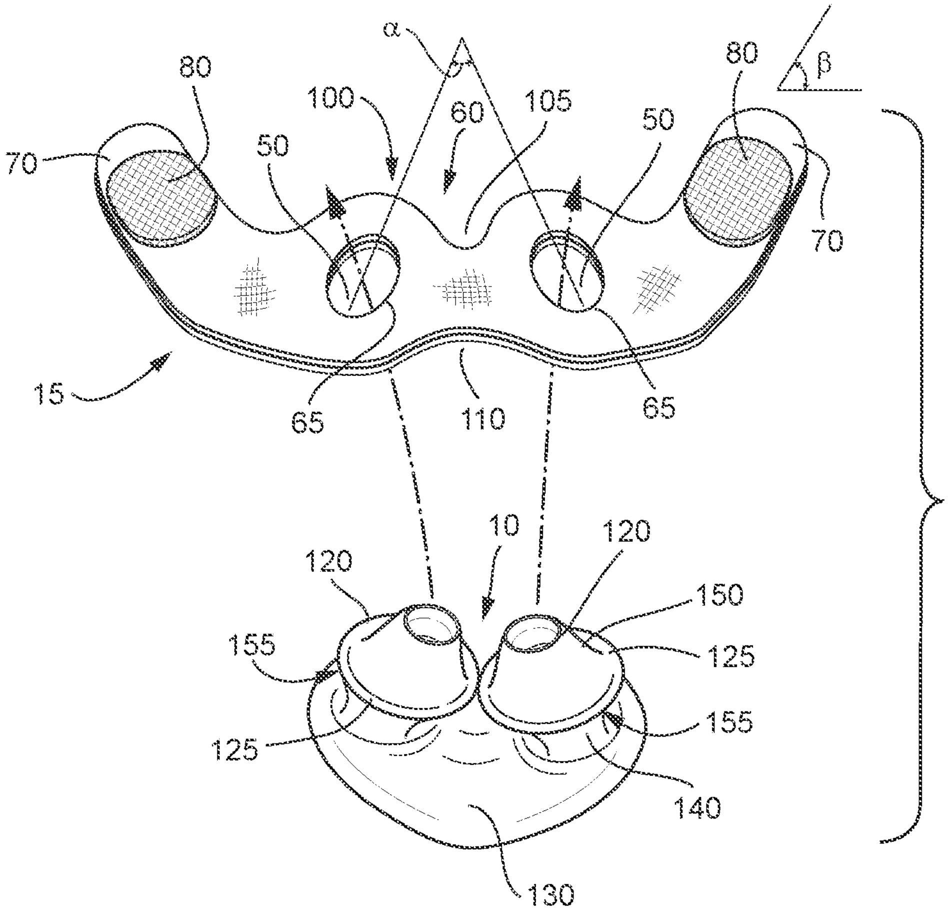
FIG. 6 is an exploded view of the nasal seal and primary headgear subassembly shown in FIG. 5 (with a variant of the primary headgear)

At least an upper or front portion 100 of a perimeter of the center section 60 is formed to follow the general shape of the apertures 50, so as to form a gap 105 between the apertures. The at least one arm 70 may be angled or oriented towards the front or upper portion 100. In the example of FIG. 6, the at least one arm is curved or curled in towards an upper portion of the center section.

A lower portion 110 of a perimeter is cut out or arc shaped to accommodate the patient's septum or top lip. Preferably, lower portion 110 may avoid or substantially avoid positioning between the mask and the patient's top lip. This arrangement may permit the mask to rest on the patient's top lip, and therefore align with the patient's nares. Alternatively, this arrangement may prevent the mask from tilting towards the patient's nose tip and away from the top lip or shifting the mask in the superior direction of the patient's nose, as the lower portion may contacting the patient's top lip and then the mask thereby offsetting the position of the mask. In general the lower or rear portion may be said to have a generally concave shape, e.g., FIGS. 10-18 and 20-22. Lower portion may have any other shape adapted to avoid the patient's top lip, for example the lower portion may comprise a slit or perforation.

An upper portion of the center section may include a raised flap 115 (FIGS. 1-4 and 17-19) to cover the patient's nares and/or portion of nasal seal in use, and/or to support the nasal seal. Raised flap 115 may be substantially curved or wrapped around the patient's nose tip. This may be achieved by flexing the material around the patient's nose tip. Alternatively, raised flap may comprise a dart and stitched portion, the dart and stitching adapted to provide the raised flap with a three dimensional curvature.

Nozzles

The primary headgear 115 may include a pair of apertures 50 provided in the center section 60, and the nasal seal 10 may be in the form of a pair of generally hollow nozzles 120, prongs or puffs that extend though respective ones of the pair of apertures 50. The nozzles 120, e.g., the widest parts 125 have a cross sectional size that is greater than a cross sectional size of the apertures 50 (in at least one orientation). The apertures 50 may be round or the apertures may be oval and have major axes that converge towards one another at an angle X of about 15°-45°, e.g., 30°, in a direction oriented towards the front side 100 of the primary headgear (FIG. 6).

The nasal pillows may be as disclosed, for example, U.S. Patent Application Publications 2007/0144525 A1 and 2006/0283461 A1, and International Application PCT/AU2008/001557, filed Oct. 22, 2008, the entire contents of each being incorporated herein by reference. It should also be appreciated that the nasal pillows may be as described in, for example, U.S. Pat. No. 7,318,437, the entire contents of which are incorporated herein by reference. It should further be appreciated that in addition to nasal pillows, the patient interface structure may include nasal pillows or prongs as disclosed, for example, in U.S. Pat. No. 4,782,832 (Trimble), U.S. Pat. No. 7,201,169 (Wilkie et al.), U.S. Pat. No. 7,059,328 (Wood), and WO 2000/074758 (Lovell). It should also be appreciated that the cannula(e) and/or nasal pillows or prongs may include features configured to diffuse the flow of air so that noise may be reduced. Such features are disclosed in, for example U.S. Patent Application Publication 2009/0044808 A1, and WO 2008/014543 A1, the entire contents of each being incorporated herein by reference. Alternative geometries may be possible.

The hollow nozzles 120 are made of a resilient material that may be deformable between a normal position and a compressed position. To assemble the nozzles and the primary headgear, the hollow nozzles are squeezed to resiliently compress them such that the nozzles 120 can be fit into and through the apertures 50, and the nozzles are structured to resiliently expand and return to the normal position once inserted through the apertures and released, so as to interlock the primary headgear with the nozzles.

Thus, the primary headgear, from which the nasal seal is suspended, provides at least one aperture though which at least a portion of the nasal seal is inserted with the primary headgear wrapping about at least one portion of the nasal seal in a sling-like fashion (FIG. 1). The patient interface includes an unobtrusive or low profile nasal seal that may be securely suspended from a relatively small headgear 15. The headgear and nasal seal are structured to inter-engage and/or interlace with one another, without requiring one or more separate clips to connect the headgear to the patient interface, and without requiring a frame or "shell" to which the cushion and clips are sometimes provided.

The nozzles 120 may be provided to or mounted on a common base or gusset portion 130. The nozzles 120 may be formed in one piece with the base or gusset, or they may be attachable and detachable from the base or gusset.

The center section 60 of the headgear 15 is provided or sandwiched between the nozzles 120 and the base or gusset portion.

Each nozzle includes a stalk 140 provided to the base or gusset portion and a generally cone shaped head 150 provided to a distal end of the stalk, the cone shaped head 150 extending through the respective aperture. Each cone shaped head includes a base surface 155 oriented to face the base or gusset portion 130, each base surface 155 being structured to engage the respective rim 65 (FIG. 6) in an assembled and suspended condition. The arms 70 are adjusted relative to the pad 20 to maintain the nasal seal in close proximity contact with the patient's nares, while also maintaining contact between the base surface 155 and rims 65.

Secondary Headgear

It may be desirable to provide fastening arrangements in addition to the primary headgear 15 and/or adhesive or adhesive pad 20 for positioning and stabilizing the patient interface structure in engagement with the patient's face. The use of additional fastening arrangements, or materials, permit the position of the patient interface structure and/or the position of the fastening arrangement to be adjusted to provide a comfortable fit while providing efficient therapy via the flow of breathable gas. The secondary headgear may assist in counteracting tube drag forces and thereby stabilize the seal in position on the patient's face.

Figure 7:
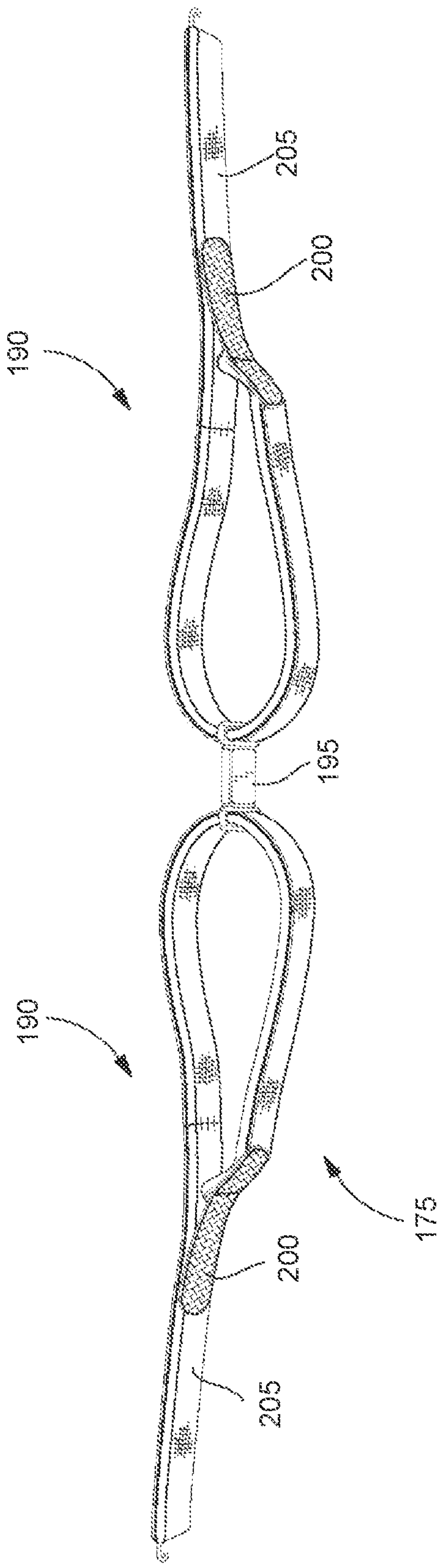
FIG. 7 is a top perspective view of an optional secondary headgear for a patient interface according to an example of the present technology.
Figure 8:
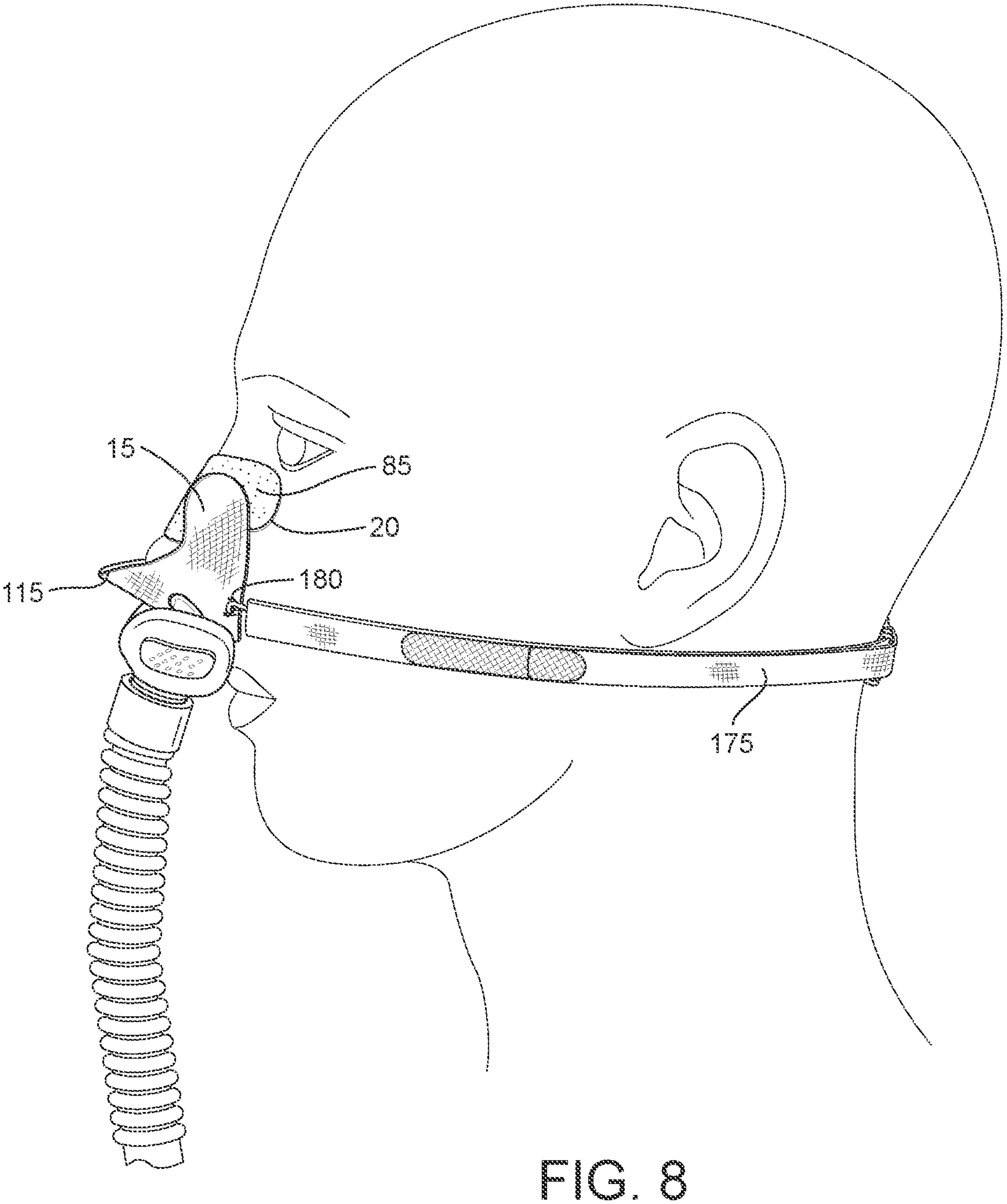
FIG. 8 is a side view of a variant of the patent interface system of FIG. 1 and the secondary headgear of FIG. 7 in an operational position on a model patient's head.
Figure 9:
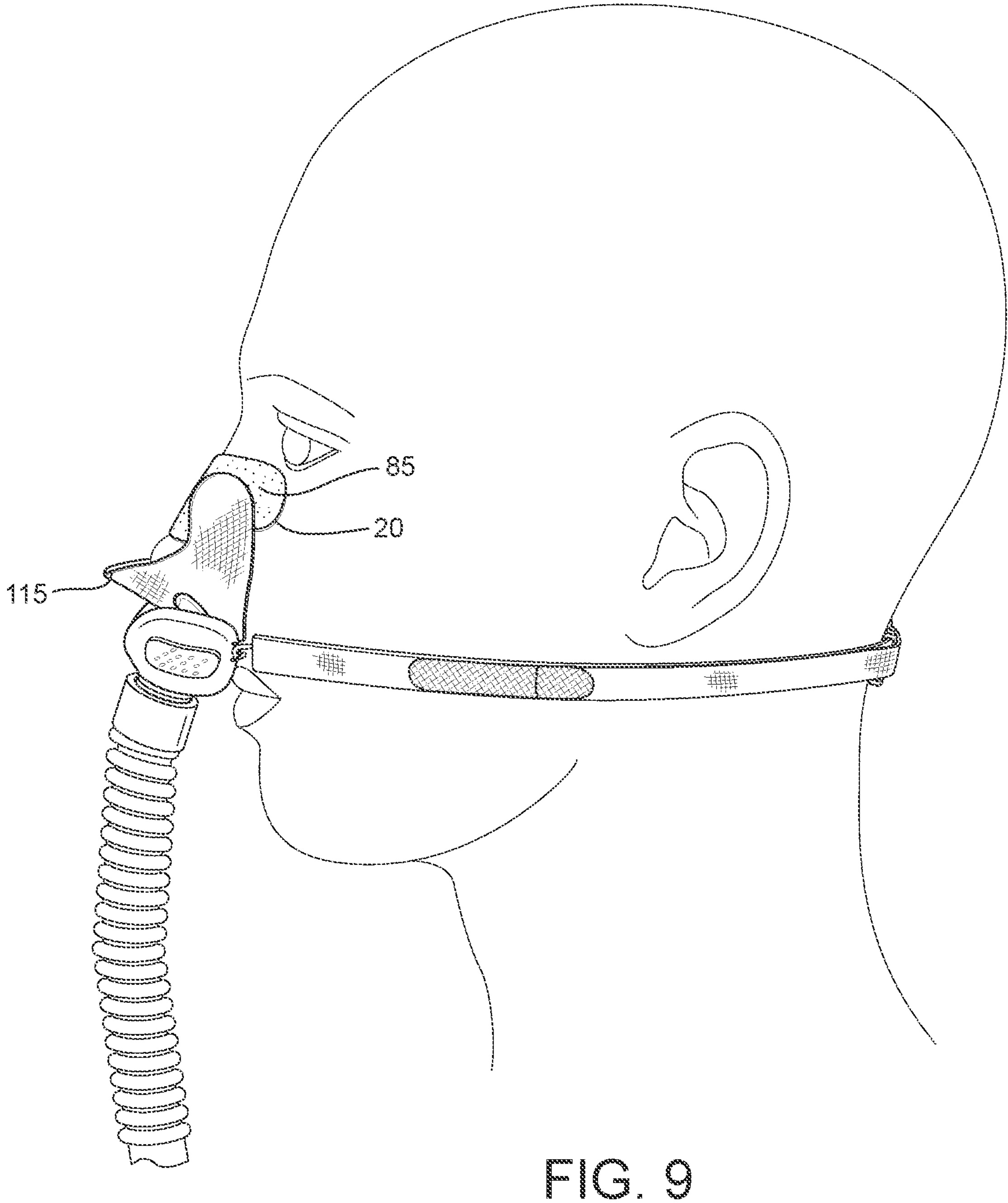
FIG. 9 is a side view of a variant of the patent interface system of FIG. 1 and the secondary headgear of FIG. 7 in an operational position on a model patient's head.
Figure 10:
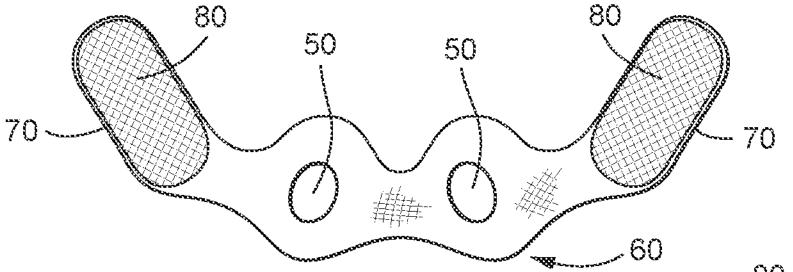
FIGS. 10-21 are top views showing a plurality of small primary headgears according to examples of the present technology.
Figure 11:
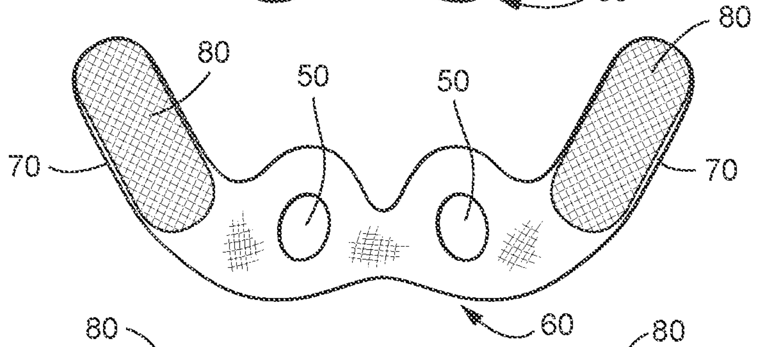

For example, while the patient interface system of FIGS. 1-3 may be secured to the patient's face using the primary headgear 15 (optionally in conjunction with the adhesive pad 20), the system may include further structure to better ensure that the nasal seal remain in sealing contact with the patient's airways. For example, the patient interface may include a secondary headgear 175 (FIG. 7). As shown in FIGS. 8-9, the secondary headgear 175 may extend around the back of the patient's head and/or underneath the patient's ears. For example, the secondary headgear 175 is dimensioned and configured to extend below the ears of the patient in use.

The secondary headgear 175 may be connected to or interact with the remainder of the system in a number of different manners.

As best shown in FIG. 7, the secondary headgear 175 includes two adjustable length portions 190 connected by a buckle 195. Each length adjustable portion includes a hook portion 200 and a loop portion 205. One or more adjustable length portions are also possible.

In an alternative shown in FIG. 8, the secondary headgear 175 may be connected to laterally spaced portions of the primary headgear 15, e.g., by placing hooks 180 on the primary headgear.

For example, as shown in FIG. 9, the secondary headgear 175 is connected to lateral side portions or connectors of the nasal seal. Such connectors may be like those described in relation to WO 2009/052560, published Apr. 30, 2009, incorporated herein by reference in its entirety. In an alternative, the secondary headgear may have one end that is integral with or in one piece with the nasal seal, and another end that can be connected and disconnected relative to the nasal seal.

The primary and secondary headgears 15, 175 may be separate, integrally formed and/or connectable with one another, or they may be formed in one piece with one another.

Nares Seal to Encompass Both Nasal Openings/Nares

The nasal seal may be in the form of a nares seal portion to substantially surround both nasal openings of the patient. The nasal seal may include a stub that extends through the at least one aperture of the primary headgear such that a junction region formed between the seal portion and the stub engages the rim.

FIGS. 22-25 show another example of the present technology, which also includes a patient interface system including a nasal seal 10 and a primary headgear 15 that is suspended from the patient's face by an adhesive pad 20 adhered to the nasal bridge region of the patient's face. However, the nasal seal 10 is in the form of a nares seal that seals around both nares in the small region between or in the vicinity of the upper lip and the tip of the user's nose, as described in relation to PCT/AU2010/00684, incorporated herein by reference in its entirety.

Figure 23:
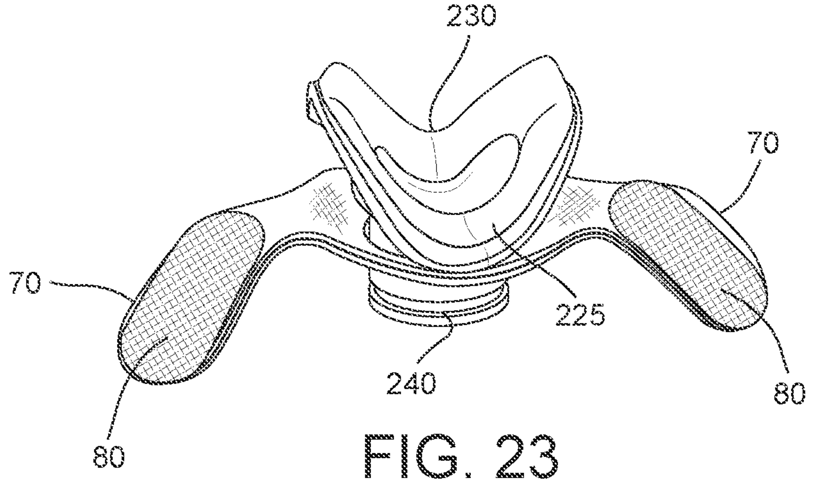
FIG. 23 is a top perspective view of the nasal seal and primary headgear subassembly shown in FIG. 22.
Figure 24:
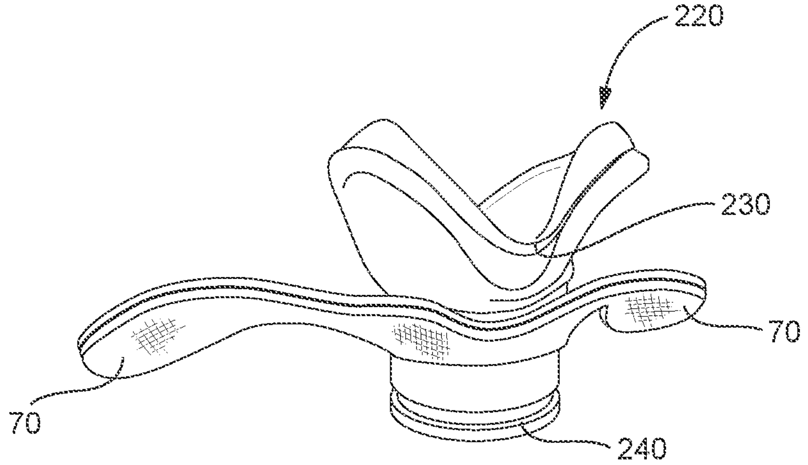
FIG. 24 is rear perspective view thereof.
Figure 25:
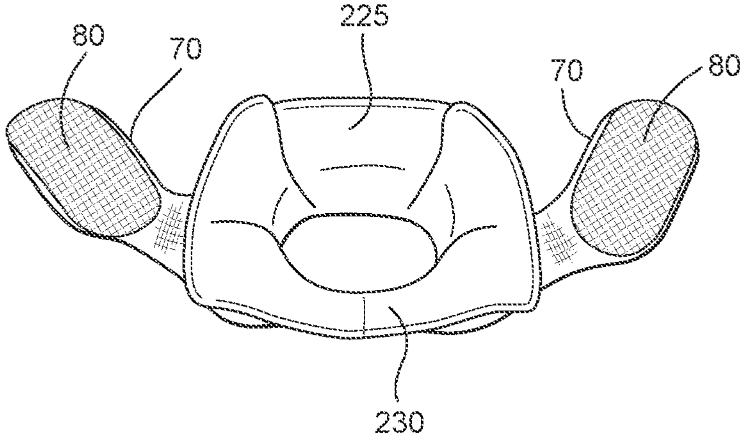
FIG. 25 is top view thereof.

Nasal seal includes a face contacting side 220. FIG. 23-25 show the nasal seal and primary headgear in various orientations, to clearly show a nares portion 225 of the seal that engages with the nares and an upper lip portion 230 that engages with the upper lip. Nasal seal also includes an opposite side that includes a stub 240 for connection to an elbow 250 or air delivery tube 255 that delivers gas at pressures of up to 2-40 cm $H_2O$, e.g., appropriate for treatment of respiratory or sleep related illness.

Figure 15:
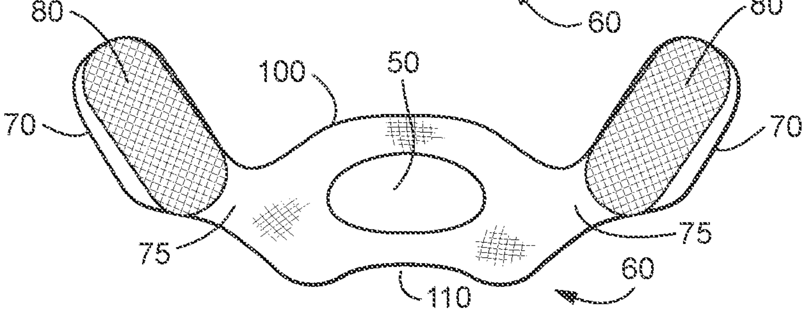
Figure 16:
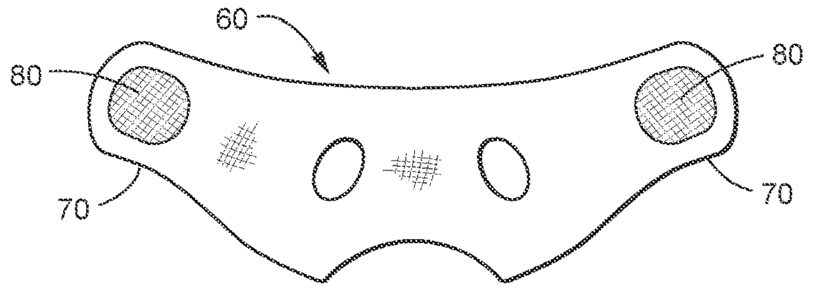
Figure 17:
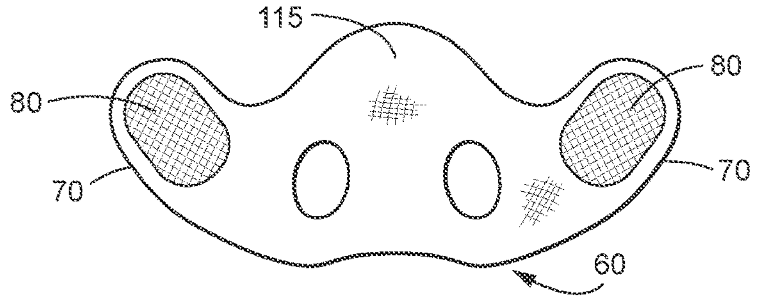
Figure 18:
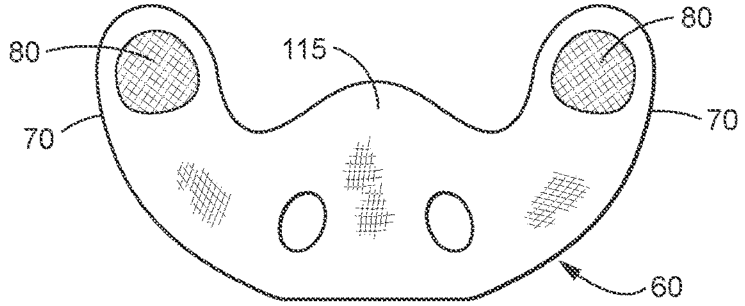
Figure 19:
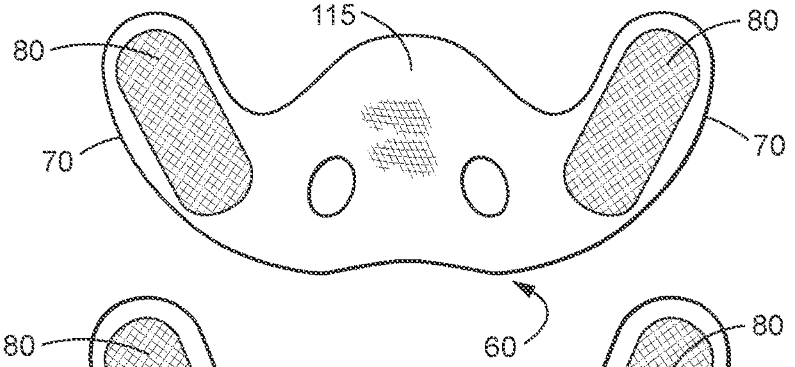
Figure 20:
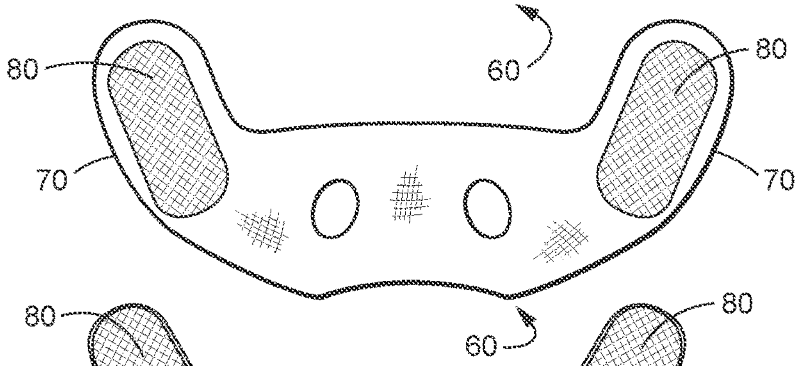
Figure 21:
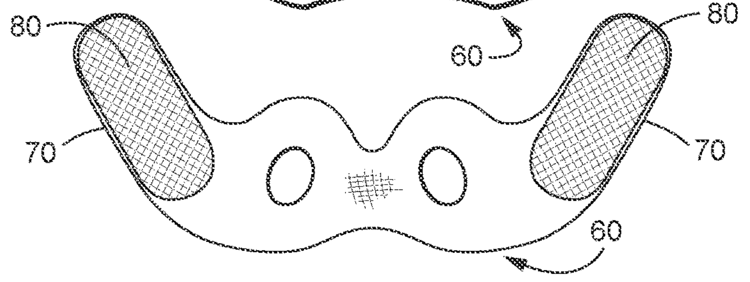
Figure 22:
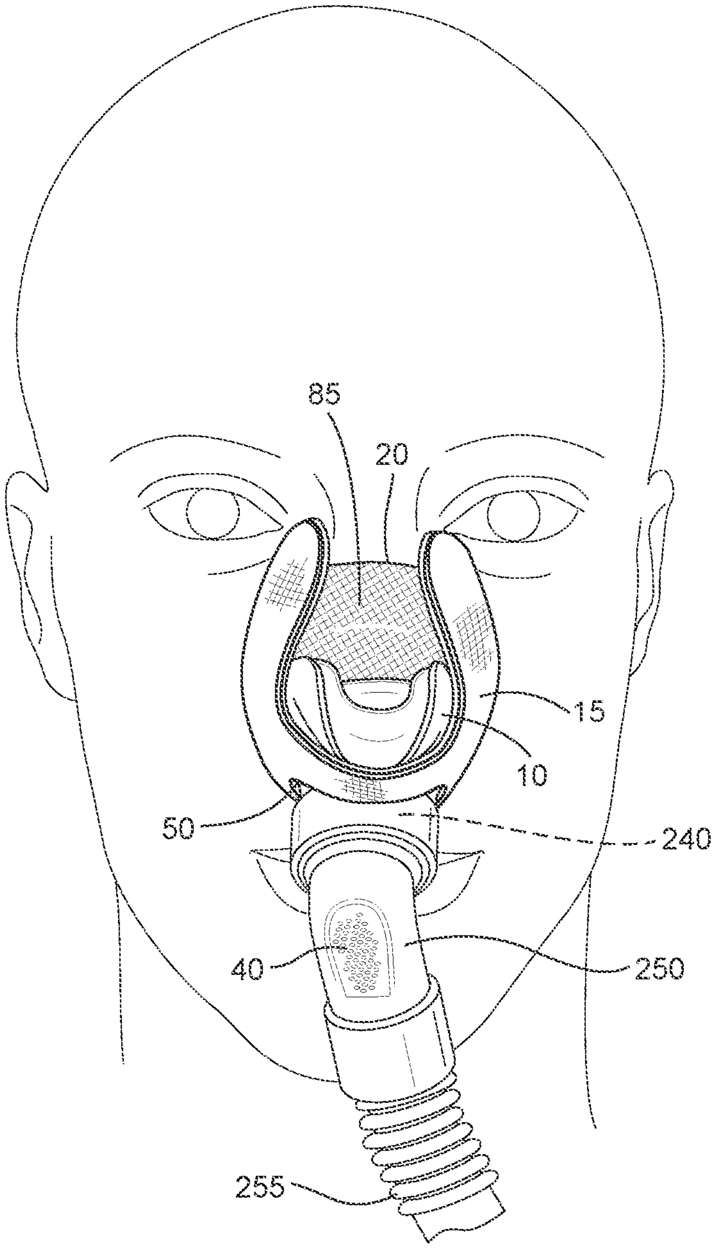
FIG. 22 is a front view of a patient interface system according to an example of the present technology in an operative position on a model patient's head in use.

The primary headgear 15 may include a center section that includes only a single aperture 50 (FIGS. 15 and 22) though which the stub 240 extends. The aperture may be oval or approximately oval and extends in a width-wise direction of the center section. As shown in FIG. 15, a front perimeter portion 100 of the center section 60 may be shaped to match the oval shaped aperture. A rear perimeter portion 110 of the center section 60 is concave adjacent the aperture (to accommodate the septum/upper lip).

While the technology has been described in connection with what are presently considered to be the most practical and preferred examples, it is to be understood that the technology is not to be limited to the disclosed examples, but on the contrary, is intended to cover various modifications and equivalent arrangements included within the spirit and scope of the technology. Furthermore, each individual component of any given assembly, one or more portions of an individual component of any given assembly, and various combinations of components from one or more embodiments may include one or more ornamental design features. In addition, while the technology has particular application to patients who suffer from OSA, it is to be appreciated that patients who suffer from other illnesses (e.g., congestive heart failure, diabetes, COPD, morbid obesity, stroke, barriatric surgery, etc.) can derive benefit from the above teachings. Moreover, the above teachings have applicability with patients and non-patients alike in non-medical applications.

What is claimed is:

1. A patient interface system comprising:

a nasal seal of flexible material configured to sealingly engage a patient's face and communicate with at least one airway of the patient, the nasal seal forming an air flow path to said at least one airway of the patient; and a primary headgear to which the nasal seal is removably attached, said primary headgear including a fabric and/or textile material connected to at least a portion of the nasal seal, with the primary headgear configured to be removably attachable to an adhesive strip positioned on the patient, wherein the primary headgear comprises a reinforcing layer at an interface between the primary headgear and the nasal seal that resists deformation and/or tearing, wherein the air flow path extends through the interface between the primary headgear and the nasal seal when the nasal seal and the primary headgear are attached to each other, and wherein a central portion of a surface of the primary headgear that is configured to engage the patient's upper lip has a concave shape so that the primary headgear engages the patient's upper lip while avoiding contact with the patient's septum, in use.

2. The patient interface system of claim 1, wherein the primary headgear is flexible.

3. The patient interface system of claim 1, wherein the primary headgear includes a laminate that has a soft first inner layer to face the patient and a second outer layer opposite to the first inner layer.

4. The patient interface system of claim 1, wherein the reinforcing layer extends at least partially around the interface between the primary headgear and the nasal seal.

5. The patient interface system of claim 1, wherein the nasal seal comprises a nares seal portion configured to substantially surround both nasal openings of the patient, and a stub that extends through an aperture of the primary headgear.

6. The patient interface system of claim 1, further comprising a pair of apertures provided in a center section of the primary headgear, and the nares seal comprises a pair of generally hollow nozzles that extend through respective ones of the pair of apertures.

7. The patient interface system of claim 6, wherein the nozzles have a cross sectional size that is greater than a cross sectional size of the apertures in at least one dimension.

8. The patient interface system of claim 6, wherein:

the nozzles are made of a resilient material that is deformable between a normal position and a compressed position, the nozzles and the primary headgear are configured to be assembled to each other by inserting the nozzles through the apertures and interlock with each other after the nozzles have passed through the apertures, and wherein the nozzles are configured to compress to the compressed position while passing through the apertures and return to the normal position after passing through the apertures.

9. The patient interface system of claim 6, wherein the apertures are round.

10. The patient interface system of claim 6, wherein the apertures are oval and have major axes that converge towards one another in a direction oriented towards a front side of the nasal seal.

11. The patient interface system of claim 6, wherein the concave shape is formed on an anterior edge of the primary headgear and faces away from the pair of apertures provided in a center section of the primary headgear.

12. The patient interface system of claim 1, wherein the reinforcing layer has a torus or donut shape.

13. A patient interface system comprising:

a nasal seal of flexible material configured to sealingly engage a patient's face and communicate with at least one airway of the patient, the nasal seal forming an air flow path to said at least one airway of the patient; and a primary headgear including a section having at least one aperture through which at least a portion of the nasal seal extends, wherein the nasal seal is positively located against a rim surrounding each of the at least one aperture, wherein each rim comprises a reinforcing structure that resists deformation and/or tearing and extends at least partially around the respective rim, wherein the air flow path extends through the at least one aperture when the nasal seal and the primary headgear are attached to each other, and wherein a central portion of a surface of the primary headgear that is configured to engage the patient's upper lip has a concave shape so that the primary headgear engages the patient's upper lip while avoiding contact with the patient's septum, in use.

14. The patient interface system of claim 13, wherein the primary headgear includes a fabric and/or textile.

15. The patient interface system of claim 13, further comprising a secondary headgear to extend around the back of the patient's head.

16. The patient interface system of claim 15, wherein the secondary headgear is configured to extend below the ears of the patient in use and is connectable to one or more lateral side portions and/or connectors of the nasal seal, and wherein at least one end of the secondary headgear includes a hook to be secured with a corresponding structure on the nasal seal.

17. The patient interface system of claim 15, wherein the secondary headgear is connected to lateral side portions of the primary headgear and includes at least one adjustable length portion connected by a buckle.

18. The patient interface system of claim 15, wherein the primary and secondary headgears are integrally formed with one another, or are formed in one piece with one another.

19. The patient interface system of claim 13, wherein each reinforcing structure comprises a torus or donut shape.

20. The patient interface system of claim 13, wherein the concave shape is formed on an anterior edge of the primary headgear and faces away from the at least one aperture in the primary headgear.

* * * * *